United States Patent
Fukuzawa et al.

(10) Patent No.: US 8,063,384 B2
(45) Date of Patent: Nov. 22, 2011

(54) DETECTION SYSTEM AND PROBE THEREFOR

(75) Inventors: Takashi Fukuzawa, Tokyo (JP); Jun Yamaguchi, Tokyo (JP)

(73) Assignee: Nippon Sheet Glass Company, Limited, Tokyo (JP)

( * ) Notice: Subject to any disclaimer, the term of this patent is extended or adjusted under 35 U.S.C. 154(b) by 279 days.

(21) Appl. No.: 12/438,536

(22) PCT Filed: Nov. 20, 2007

(86) PCT No.: PCT/JP2007/072884
§ 371 (c)(1),
(2), (4) Date: Feb. 23, 2009

(87) PCT Pub. No.: WO2008/066054
PCT Pub. Date: Jun. 5, 2008

(65) Prior Publication Data
US 2010/0224793 A1 Sep. 9, 2010

(30) Foreign Application Priority Data
Nov. 28, 2006 (JP) ................................. 2006-320146

(51) Int. Cl.
*G01J 1/58* (2006.01)
(52) U.S. Cl. .................................. 250/458.1; 250/459.1
(58) Field of Classification Search ............... 250/458.1, 250/459.1
See application file for complete search history.

(56) References Cited

U.S. PATENT DOCUMENTS

| | | | |
|---|---|---|---|
| 5,142,155 A | 8/1992 | Mauze et al. | |
| 5,294,799 A | 3/1994 | Aslund et al. | |
| 5,674,698 A | 10/1997 | Zarling et al. | |
| 6,707,556 B2 | 3/2004 | Turner et al. | |
| 2004/0119976 A1* | 6/2004 | Faupel et al. | 356/337 |
| 2004/0197267 A1* | 10/2004 | Black et al. | 424/9.6 |
| 2006/0109465 A1 | 5/2006 | Fukuzawa et al. | |
| 2006/0238858 A1 | 10/2006 | Kawasaki et al. | |
| 2007/0064228 A1* | 3/2007 | Tartakovsky et al. | 356/317 |
| 2007/0098594 A1* | 5/2007 | Elkin et al. | 422/64 |

(Continued)

FOREIGN PATENT DOCUMENTS

JP 06-027110 A 2/1994

(Continued)

OTHER PUBLICATIONS

English Language International Search Report dated Feb. 19, 2008 issued in parent Appln. No. PCT/JP2007/072884.

(Continued)

*Primary Examiner* — Mark R Gaworecki
(74) *Attorney, Agent, or Firm* — Holtz, Holtz, Goodman & Chick, PC

(57) ABSTRACT

There is provided a detection system capable of simultaneously detecting a plurality of fluorescences or phosphorescences having different dominant wavelengths generated from a minute region and a probe therefor. A fluorescence detection system includes a probe having a lens and optical fibers and arranged on one end thereof. The probe receives excitation light with a dominant wavelength and excitation light with a dominant wavelength at one end of the lens and converges the excitation lights at the solution containing Cy3 and Cy5 in a channel inside a microchemical chip and the probe receives fluorescence with a dominant wavelength and fluorescence with a dominant wavelength at the other end of the lens and converges the fluorescences at the tips of the optical fibers.

9 Claims, 11 Drawing Sheets

U.S. PATENT DOCUMENTS

2008/0030718 A1    2/2008   Tamai et al.
2009/0153852 A1*   6/2009   Rensen .................... 356/300

FOREIGN PATENT DOCUMENTS

| | | |
|---|---|---|
| JP | 8-506419 A | 7/1996 |
| JP | 2003-177096 A | 6/2003 |
| JP | 2005-030830 A | 2/2005 |
| JP | 2007-041510 A | 2/2005 |
| JP | 2006-234794 A | 9/2006 |
| JP | 2006-317282 A | 11/2006 |
| WO | WO 2006/080556 A1 | 8/2006 |

OTHER PUBLICATIONS

U.S. Appl. No. 12/438,722, filed Feb. 24, 2009, "Fluorescence Detection System", Takashi Fukuzawa.

International Report on Patentability and Written Opinion of the International Searching Authority dated Jun. 11, 2009 (7 pages), issued in counterpart International Application No. PCT/JP2007/072884.

* cited by examiner

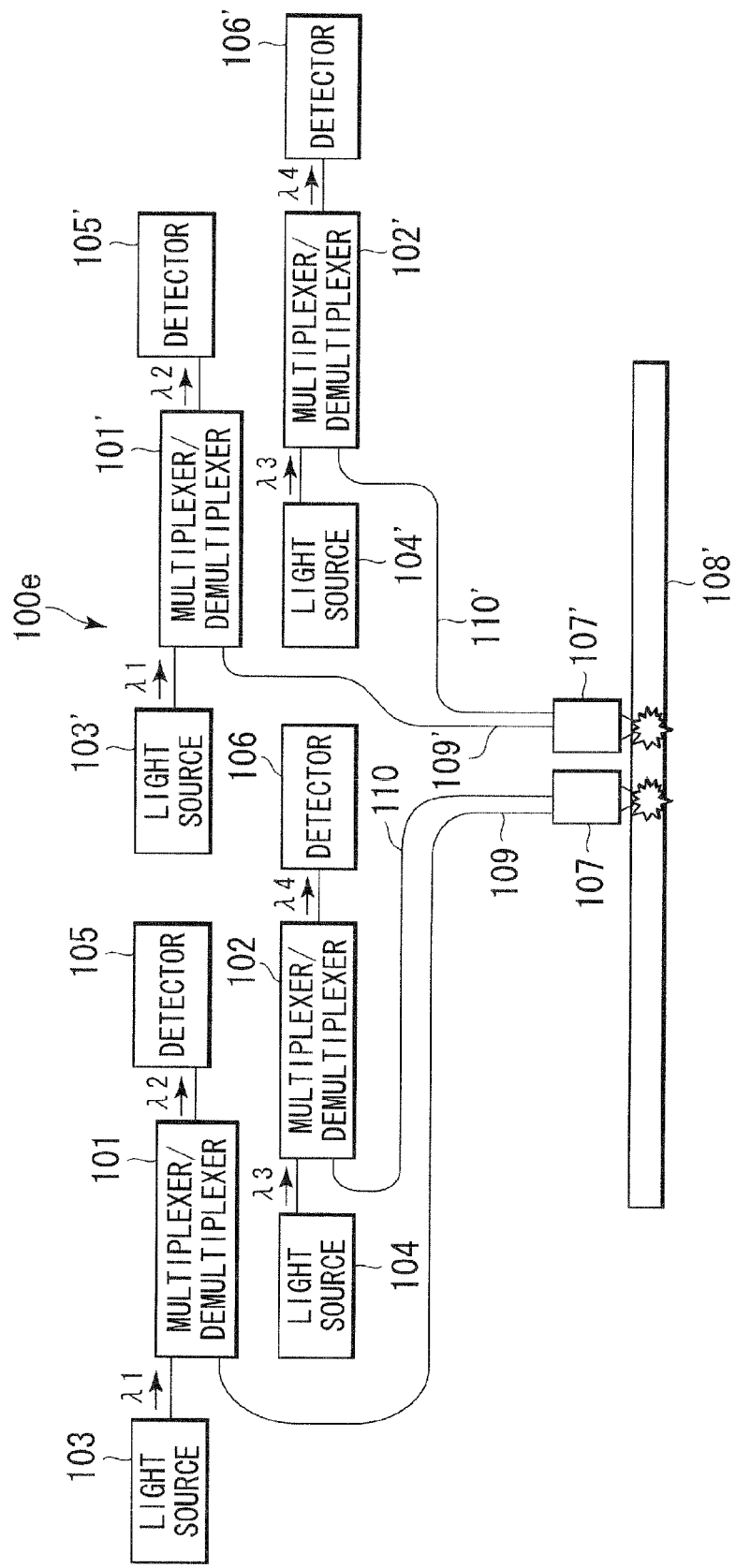

DETECTION SYSTEM AND PROBE THEREFOR

This application is a U.S. National Phase Application under 35 USC 371 of International Application PCT/JP2007/072884 filed Nov. 20, 2007.

TECHNICAL FIELD

The present invention relates to a detection system and a probe therefor, and more particularly, to a detection system and a probe therefor which are used to detect fluorescence and phosphorescence in a small measurement region.

BACKGROUND ART

In a microchemical system, a very small amount of samples needs to be detected and analyzed with high sensitivity after chemical treatment has been performed using a microwell, a microchemical chip and an electrophoretic chip. Until now, in the microchemical system, there has been often used a detection method using fluorescence and phosphorescence.

As shown in FIG. 9, as a conventional technique, for example, there has been known a method of cause a plurality of laser beams to travel through a space to irradiate a measurement region therewith at the time of detecting fluorescence and phosphorescence generated from a sample flowing through a microchemical chip.

This method, however, some distance is required in order to cause the laser beams to travel, extending the laser beam by diffraction, which the size of a focal point cannot be reduced to substantially 0.5 mm or less, resultantly, a minute region cannot be detected. Furthermore, this method adjusts a position irradiated with the laser beams by adjusting the angle of a mirror or the like, however, some distance is required in order to cause the laser beams to travel, so that a subtle angular displacement occurring at the time of adjusting the angle causes a positional displacement, making it difficult to adjust the position and there is a problem that the method is susceptible to vibration.

This method is capable of irradiating the same minute region with a plurality of laser beams, however, as stated above, it is basically difficult for the method to adjust the position, requiring a very complicated optical system. When a plurality kinds of substances generating fluorescence or phosphorescence at a plurality of points are simultaneously measured, this method scans laser beams to quasi-simultaneously measure the substances. The quasi-simultaneous measurement, however, needs a more complicated optical system. In addition, a short irradiation time significantly reduces sensitivity.

As shown in FIG. 10, as a method of solving the problem, there has been known a method in which a laser beam and fluorescence (or phosphorescence) are propagated thorough an optical fiber and the laser beam is focused to a measuring region by a microlens to detect the fluorescence (phosphorescence) (refer to, for example, Japanese Laid-Open Patent Publication (Kokai) No. 2005-30830).

However, the above method in the conventional art causes the following problem at the time of measuring concentration and state of a plurality kinds of substances generating fluorescence or phosphorescence in solution.

In the case where the above substances are irradiated with excitation light having a different dominant wavelength to excite the substances and fluorescence (phosphorescence) having a different dominant wavelength generated from solution thereby is detected, the method in the conventional art requires two detection systems of FIG. 10 as shown in FIG. 11. In the system, the focal position of each excitation light is displaced due to a width of the lens used for focusing. Using a small lens such as a microlens for focusing displaces a focal position by 2 mm to 3 mm. For this reason, the detection system shown in FIG. 11 cannot be used to detect fluorescence (phosphorescence) in solution containing the above substances which is contained in the same micro well.

The object of the present invention is to provide a detection system capable of simultaneously detecting a plurality of fluorescences or phosphorescences having different dominant wavelengths and generated from a minute region and a probe therefor.

DISCLOSURE OF THE INVENTION

To attain the above object, according to a first aspect of the present invention, there is provided a detection system in which a plurality kinds of substances in solution or solid is irradiated with excitation lights with dominant wavelengths different from each other so as to be excited to generate fluorescence or phosphorescence and the fluorescence or phosphorescence with dominant wavelengths different from each other generated from the solution or solid in a relaxation process is detected to measure the concentration or state of the plurality kinds of substances, the detection system comprising a probe including a lens and at least one optical fiber arranged on one end thereof, wherein the probe receives the excitation lights at one end of the lens and converges the excitation lights at the solution or the solid, and the probe receives the fluorescence or phosphorescence at the other end of the lens and converges the fluorescence or phosphorescence at the tips of the optical fibers propagating the excitation lights attributed to the occurrence of the fluorescence or phosphorescence.

In the first aspect of the present invention, it is preferable that the lens is formed of a single lens or a plurality of lenses arranged on the same optical axis.

In the first aspect of the present invention, it is preferable that the at least one optical fiber is formed of a plurality of optical fibers propagating the fluorescence or phosphorescence with dominant wavelengths different from each other and the plurality of optical fibers propagates the excitation lights with dominant wavelengths different from each other to the one end of the lens.

In the first aspect of the present invention, it is preferable that the plurality of optical fibers propagates the excitation lights and the fluorescence or phosphorescence to detectors different from each other through multiplexers/demultiplexers adapted to separate the excitation lights and the fluorescence or phosphorescence.

In the first aspect of the present invention, it is preferable that the detection system further comprises a light emitting control unit adapted to control the light emitting timing of the excitation lights to detect the fluorescence or phosphorescence based on the light emitting timing.

In the first aspect of the present invention, it is preferable that the at least one optical fiber is formed of one optical fiber propagating all the excitation lights to the one end of the lens.

In the first aspect of the present invention, it is preferable that the optical fiber is connected to a plurality of detectors through a multiplexer/demultiplexer adapted to separate the propagated fluorescence or phosphorescence by dominant wavelength.

In the first aspect of the present invention, it is preferable that the detection system propagates all the fluorescences or phosphorescences to one detector.

In the first aspect of the present invention, it is preferable that the detection system further comprises a light emitting frequency control unit adapted to control respectively the light emitting frequencies of the excitation lights to detect the fluorescence or phosphorescence propagated to the one detection unit based on the light emitting frequencies.

To attain the above object, according to a second aspect of the present invention, there is provided a detection system in which a plurality kinds of substances in solution is irradiated with excitation lights with dominant wavelengths different from each other so as to be excited to generate fluorescence or phosphorescence and fluorescence or phosphorescence with dominant wavelengths different from each other generated from the solution in a relaxation process is detected to measure the concentration or state of the plurality kinds of substances, the detection system comprising a probe including a lens and at least two optical fibers arranged on one end thereof, wherein the probe receives one of the excitation lights at one end of the lens through one of the optical fibers and converges the excitation lights at the solution, and the probe receives the fluorescence or phosphorescence generated by irradiating the solution with the one of the excitation lights at the other end of the lens and converges the fluorescence or phosphorescence at the tips of the optical fibers propagating the excitation lights attributed to the occurrence of the fluorescence or phosphorescence.

In the second aspect of the present invention, it is preferable that the lens is formed of a single lens or a plurality of lenses arranged on the same optical axis.

To attain the above object, according to a third aspect of the present invention, there is provided a probe used in a detection system in which a plurality kinds of substances in solution or solid is irradiated with excitation lights with dominant wavelengths different from each other so as to be excited to generate fluorescence or phosphorescence and the fluorescence or phosphorescence with dominant wavelengths different from each other generated from the solution or solid in a relaxation process is detected to measure the concentration or state of the plurality kinds of substances, the probe including a lens and at least one optical fiber arranged on one end thereof, wherein the probe receives the excitation lights at one end of the lens and converges the excitation lights at the solution or the solid, and the probe receives the fluorescence or phosphorescence at the other end of the lens and converges the fluorescence or phosphorescence at the tips of the optical fibers propagating the excitation lights attributed to the occurrence of the fluorescence or phosphorescence.

In the third aspect of the present invention, it is preferable that the lens is formed of a single lens or a plurality of lenses arranged on the same optical axis.

In the third aspect of the present invention, it is preferable that the at least one optical fiber is formed of a plurality of optical fibers propagating the fluorescence or phosphorescence with dominant wavelengths different from each other and the plurality of optical fibers propagates the excitation lights with dominant wavelengths different from each other to the one end of the lens.

In the third aspect of the present invention, it is preferable that the at least one optical fiber is formed of two optical fibers and the two optical fibers include a first optical fiber propagating fluorescence or phosphorescence with a first dominant wavelength generated from one of the plurality kinds of substances and a second optical fiber propagating fluorescence or phosphorescence with a second dominant wavelength generated from another of the plurality kinds of substances.

In the third aspect of the present invention, it is preferable that the chromatic aberration of the excitation light converged by the lens is less than 0.1 mm.

In the third aspect of the present invention, it is preferable that anti-reflection coating is applied on the tip of the at least one optical fiber.

In the third aspect of the present invention, it is preferable that the tip of the at least one optical fiber is fabricated such as to form an angled facet.

In the third aspect of the present invention, it is preferable that the tips of the optical fibers are fixed to abut on each other.

In the third aspect of the present invention, it is preferable that the at least one optical fiber is formed of one optical fiber propagating all the excitation lights to the one end of the lens.

In the third aspect of the present invention, it is preferable that an image in the optical fiber formed by the lens is a reduction system which is smaller than 1:1.

BRIEF DESCRIPTION OF THE DRAWINGS

FIG. 6 is a schematic block diagram showing the configuration of a fourth variation of the fluorescence detection system.

BEST MODE FOR CARRYING OUT THE INVENTION

The present inventors have dedicated themselves to study to achieve the above object and found that in a detection system in which a plurality kinds of substances in solution or solid is irradiated with excitation lights with dominant wavelengths different from each other so as to be excited to generate fluorescence or phosphorescence and the fluorescence or phosphorescence with dominant wavelengths different from each other generated from the solution or solid in a relaxation process is detected to measure the concentration or state of the plurality kinds of substances, the detection system including a probe having a lens and at least one optical fiber arranged on one end thereof, wherein the probe receives the excitation lights at one end of the lens and converges the excitation lights at the solution or the solid, and the probe receives the fluorescence or phosphorescence at the other end of the lens and converges the fluorescence or phosphorescence at the tips of the optical fibers propagating the excitation lights attributed to the occurrence of the fluorescence or phosphorescence, thereby allowing a simultaneous measurement of a plurality of fluorescences and phosphorescences with different dominant wavelengths emitted from a minute region.

The present invention has been made based on the above knowledge.

An embodiment of the present invention is described below in detail with reference to the drawings.

Figure 1:
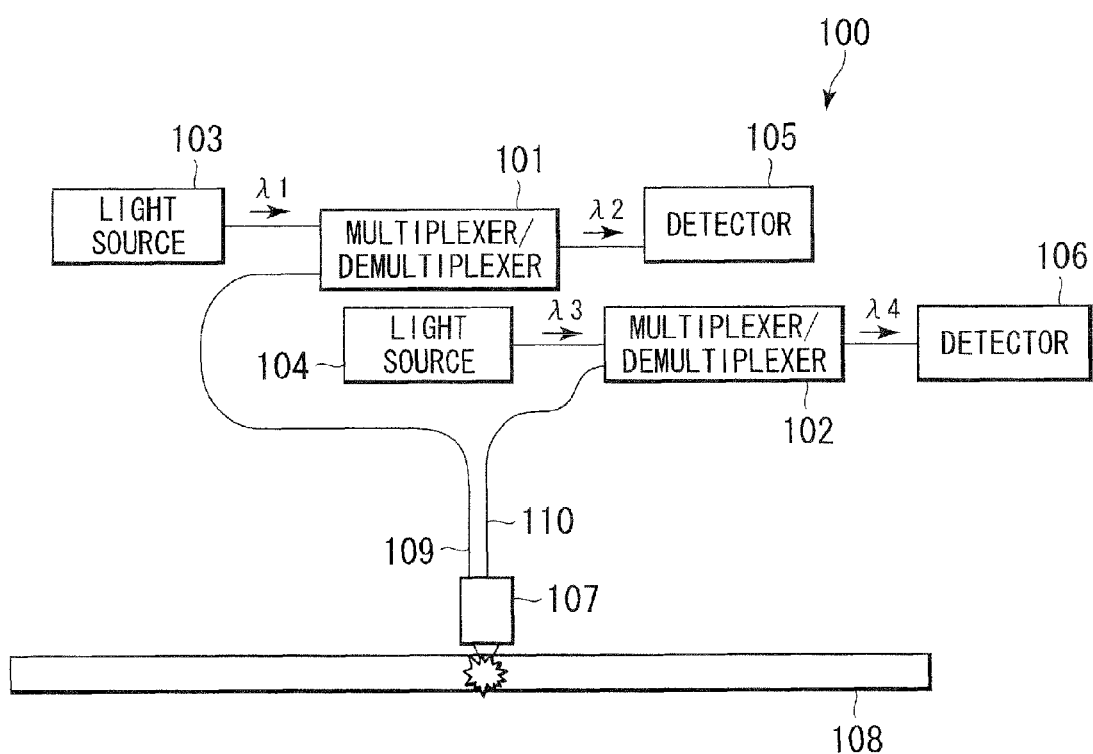
FIG. 1 is a schematic block diagram showing the configuration of a fluorescence detection system as a detection system according to the present embodiment of the present invention.

FIG. 1 is a schematic block diagram showing the configuration of a fluorescence detection system as a detection system according to the present embodiment of the present invention. In the following embodiment, there is described the case where solution containing two kinds of fluorescent substances each generating fluorescence having a different dominant wavelength is caused to flow through a channel of a microchemical chip. However, the present invention is not limited to the following embodiment as long as solution or solid containing a substance generating fluorescence or phosphorescence is irradiated with a laser beam to detect the fluorescence or phosphorescence. For example, if a sample is a solid containing a fluorescent substance, the solid is placed in a focal position of excitation light to detect the fluorescence or phosphorescence without a microchemical chip being used.

In FIG. 1, a fluorescence detection system 100 includes a microchemical chip 108 inside which a channel (a depth of 100 μm and a width of 200 μm) is formed, a light source 103 formed of an LED (NSPG500S produced by Nichia Corporation) oscillating an excitation light with a dominant wavelength $\lambda 1$ (=530 nm), a light source 104 formed of an LD (DL-5038-021 produced by SANYO Electric Co., Ltd.) oscillating an excitation light with a dominant wavelength $\lambda 3$ (=630 nm) and a probe (detection tip) 107 at one end which receives excitation light from light sources 103 and 104 through multiplexers/demultiplexers 101 and 102.

The multiplexer/demultiplexer 101 is so designed as to reflect light whose wavelength is 540 nm or less and transmit light whose wavelength is 550 nm or more. The multiplexer/demultiplexer 102 is so designed as to reflect light whose wavelength is 640 nm or less and transmit light whose wavelength is 650 nm or more.

One end of the probe 107 includes an optical fiber 109 propagating excitation light oscillated by the LED light source 103 to the probe 107 and an optical fiber 110 propagating excitation light oscillated by the laser light source 104 to the probe 107. The optical fibers 109 and 110 use a quartz step index fiber with a core diameter of 200 μm and a clad diameter of 250 μm.

Figure 2:
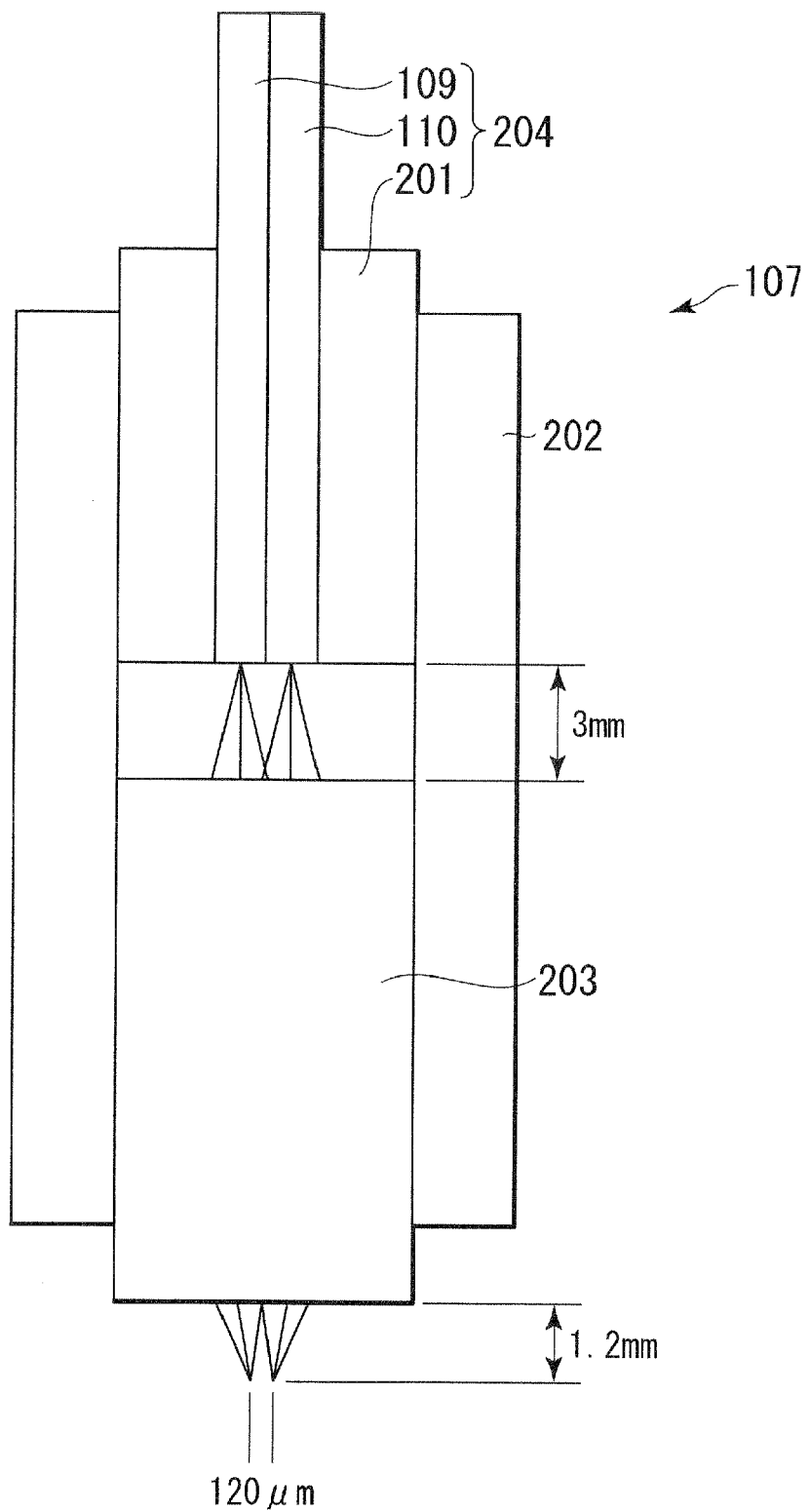
FIG. 2 is a schematic view of the configuration of the probe in FIG. 1.

The probe 107 is configured as shown in FIG. 2 so as to adjust the focal position of each excitation light to the channel inside the microchemical chip 108. Cy3 (produced by Amersham Biosciences Corp.) contained in solution in the channel inside the microchemical chip 108 generates fluorescence with a dominant wavelength $\lambda 2$ (=565 nm) when excited by excitation light with a dominant wavelength $\lambda 1$. Cy5 (produced by Amersham Biosciences Corp.) contained in solution in the channel generates fluorescence with a dominant wavelength $\lambda 4$ (=665 nm) when excited by excitation light with a dominant wavelength $\lambda 3$.

The other end of the probe 107 receives fluorescence with a dominant wavelength $\lambda 2$ and converges it to the tip of the optical fiber 109, and the other end of the probe 107 also receives fluorescence with a dominant wavelength $\lambda 4$ and converges it to the tip of the optical fiber 110. Thereby, the optical fibers 109 and 110 propagating the excitation light also propagate the fluorescence generated by irradiating the Cy2 and Cy5 with each excitation light, so that the system can be downsized. In addition, four points being the sum of the focal points of two excitation lights and the light emission points of two fluorescences are located substantially at the same position, so that not only two kinds of substances lying in a minute region can be simultaneously measured, but also the above focal points can be easily positioned in the channel inside the microchemical chip 108, which realizes the simplification of positional adjustment and the improvement of positional accuracy.

The fluorescence detection system 100 further includes a detector 105 which receives the fluorescence with a dominant wavelength $\lambda 2$ converged at the tip of the optical fiber 109 through the multiplexer/demultiplexer 101 to detect the intensity of the fluorescence and a detector 106 which receives the fluorescence with a dominant wavelength $\lambda 4$ converged at the tip of the optical fiber 110 through the multiplexer/demultiplexer 102 to detect the intensity of the fluorescence. The detectors 105 and 106 use an APD (S5843 produced by Hamamatsu Photonics K.K.).

The multiplexers/demultiplexers 101 and 102 respectively receive the excitation light from the excitation light sources 103 and 104 through the optical fibers and propagate the fluorescence to the detectors 105 and 106 through the optical fibers. As is the case with the optical fibers 109 and 110, those optical fibers use a quartz step index fiber with a core diameter of 200 μm and a clad diameter of 250 μm. Although the multiplexer/demultiplexer has been so designed as to reflect a shorter wavelength and transmit a longer wavelength herein, the multiplexer/demultiplexer may be so designed as to reflect a longer wavelength and transmit a shorter wavelength, alternatively, the multiplexer/demultiplexer may be so designed as to transmit only a specific wavelength and reflect the rest of the wavelengths. A filter may be interposed between the excitation light source and the multiplexer/demultiplexer or between the detector and the multiplexer/demultiplexer to reduce noise. The optical fiber may use a compound glass fiber, a plastic fiber, or a grated index fiber in addition to a quartz fiber. The optical fiber may have a core diameter of 100 (μm)/a clad diameter of 125 (μm), a core diameter of 62.5 (μm)/a clad diameter of 125 (μm) and a core diameter of 50 (μm)/a clad diameter of 125 (μm). The optical fiber is preferably large in core diameter.

FIG. 2 is a schematic view of the configuration of the probe 107 in FIG. 1.

In FIG. 2, the probe 107 includes the optical fibers 109 and 110, a SELFOC microlens 203 (produced by Nippon Sheet Glass Co., Ltd., SLW18-0.25p, simply referred to as "lens"), a rectangular hole micro-capillary 201 (produced by Nippon Electric Glass Co., Ltd.) with an outer diameter of 1.8 mm which adhesively secures the optical fibers 109 and 110 and a glass tube 202 with an inner diameter of 1.8 mm which secures the micro-capillary 201 and the lens 203.

The micro-capillary 201 has a rectangular hole with a long side of 0.510 mm and a short side of 0.260 mm in which two optical fibers are of aligned to align the axes thereof. The optical fibers 109 and 110 are put in the hole and adhesively secured, and their faces opposing the lens 203 are polished and then anti-reflection (AR) coating is applied there on. Thereby, the tips of the optical fibers 109 and 110 are secured to the one end of the lens 203 to abut on each other. As a result, the displacement of focal point of light outputted from the optical fibers 109 and 110 can fall within the range of approximately 0.2 mm in the direction perpendicular to the optical axis direction of the lens 203, which surely enables each excitation light to be converged in the channel of the microchemical chip formed at a width of typically 0.5 mm or less.

Thus, the optical fibers 109 and 110 adhesively secured by the micro-capillary 201 form a two-core fiber pigtail 204.

After that, the two-core fiber pigtail 204 and the lens 203 are inserted into the glass tube 202 and fixed so that a distance between the lens and the optical fibers is 3 mm. Thus, the probe 107 is formed.

The probe 107 uses the lens 203 as a reduction system. This makes a distance shorter between two focal points arranged in the direction perpendicular to the optical axis of the lens 203 than the distance (approximately 0.25 mm) between the optical fibers 109 and 110.

The displacement of focal points of excitation lights whose dominant wavelengths are different outputted from the optical fibers 109 and 110 can fall within the range of 0.1 mm in the optical axis direction of the lens 203.

The channel of the microchemical chip 108 is generally formed by wet etching, this makes it difficult to form a channel with a depth of 0.1 mm or more. For this reason, if the displacement of a focal point of each excitation light in the above optical axis, as described above, that is to say, chromatic aberration is 0.1 mm or less, each excitation light can be surely converged in the channel. In the present invention, the term "chromatic aberration" refers to a difference in which a distance between a lens end-face and a focal position is varied with an optical wavelength.

Although not shown, the end face of the two-core fiber pigtail 204 is polished with the end face tilted by approximately 8 degrees in order to prevent the excitation light from being reflected at the end faces of the optical fibers 109 and 110.

In the fluorescence detection system 100, the concentrations of Cy3 and Cy5 contained in the solution in the channel of the microchemical chip 108 were sequentially varied.

The excitation light from the light source 103 was blinked at approximately 1 kHz and the excitation light from the light source 104 was blinked at approximately 1.2 kHz. The outputs from the detectors 105 and 106 were synchronously detected by a lock-in amplifier to detect the fluorescence generated from the channel of the microchemical chip 108. Thereby, even if the concentrations of Cy3 and Cy5 contained in the solution in the channel of the microchemical chip 108 are sequentially varied, fluorescence can be detected according to change in concentration.

The detection limit of Cy3 was 1 µmol/L and that of Cy5 was 0.1 µmol/L or less, which provided good sensitivity.

Thus, according to the present embodiment, in the fluorescence detection system 100, the probe 107 including the lens 203 and the optical fibers 109 and 110 arranged on one end thereof receives the excitation light with the dominant wavelength $\lambda 1$ and the excitation light with the dominant wavelength $\lambda 3$ at one end of the lens and converges the excitation lights at the solution containing Cy3 and Cy5 in the channel of the microchemical chip 108 and, in addition, the probe 107 receives the fluorescence with the dominant wavelength $\lambda 2$ and the fluorescence with the dominant wavelength $\lambda 4$ at the other end of the lens 203 and converges the fluorescences at the tips of the optical fibers 109 and 110. This allows a simultaneous detection of the fluorescence with the dominant wavelength $\lambda 2$ and the fluorescence with the dominant wavelength $\lambda 4$ generated by the solution in the channel of the microchemical chip 108.

Figure 3:
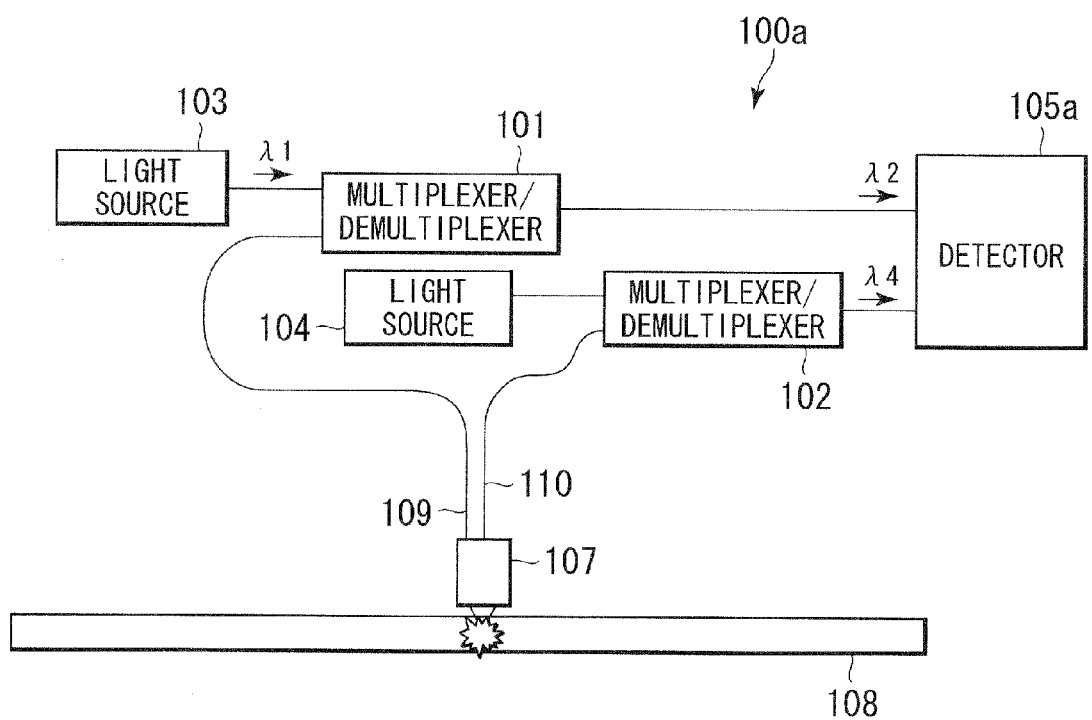
FIG. 3 is a schematic block diagram showing the configuration of a first variation of the fluorescence detection system in FIG. 1.

As a fluorescence detection system 100a shown in FIG. 3, the fluorescences with dominant wavelengths $\lambda 2$ and $\lambda 4$ from two multiplexers/demultiplexers 101 and 102 may be received by one detector 105a to simultaneously detect each fluorescence as intensity of each frequency component by Fast Fourier Transform (FFT). In this case, the detection limit of Cy3 was 1 µmol/L and that of Cy5 was 0.1 µmol/L or less, which provided good sensitivity.

Figure 4:
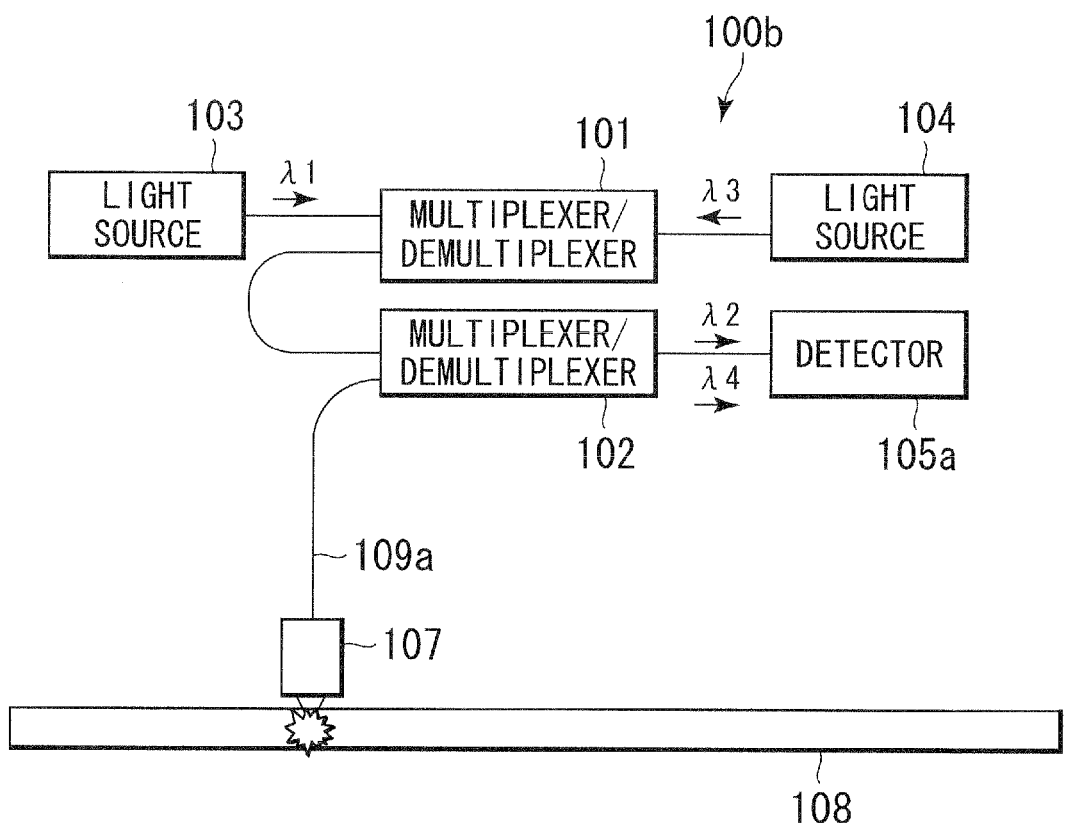
FIG. 4 is a schematic block diagram showing the configuration of a second variation of the fluorescence detection system.

Furthermore, as a fluorescence detection system 100b shown in FIG. 4, two excitation lights from the light sources 103 and 104 are combined into one optical fiber 109a to perform irradiation. Thereby, the optical fiber 109a propagating all excitation lights propagates also all fluorescences generated by irradiating the solution with the excitation lights, so that the system can be downsized.

Figure 5:
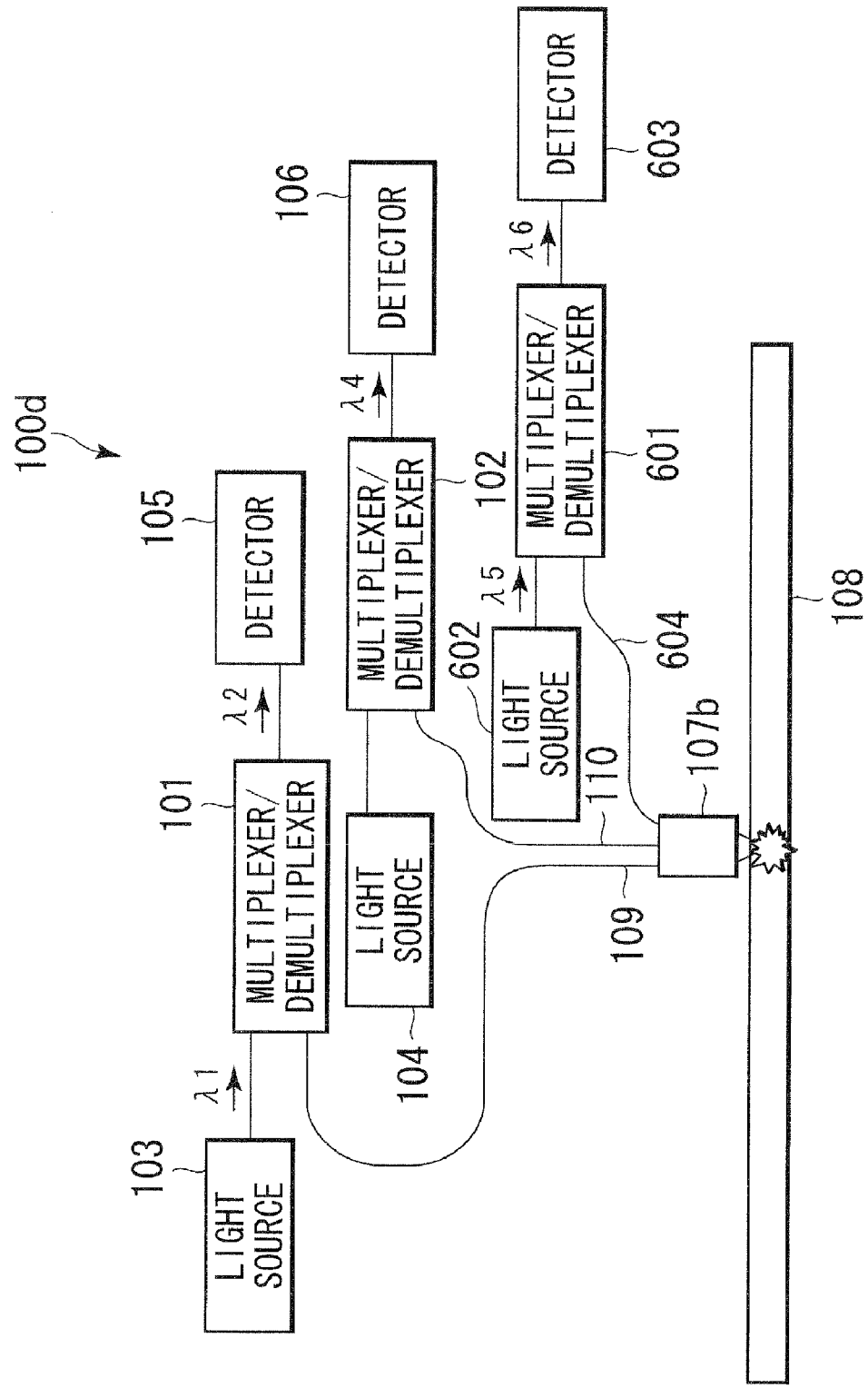
FIG. 5 is a schematic block diagram showing the configuration of a third variation of the fluorescence detection system.

Although the above fluorescence detection system has been adapted to detect fluorescence in the case where two kinds of fluorescent substances exist in the channel of the microchemical chip 108, as a fluorescence detection system 100d shown in FIG. 5, the channel of the microchemical chip 108 is irradiated with the excitation lights having three or more different dominant wavelengths to enable fluorescence to be detected in the case where three kinds or more of fluorescent substances exist in the channel.

If there are a plurality of channels in the microchemical chip 108, as a fluorescence detection system 100e shown in FIG. 6, a plurality of probes may be positioned on each channel. This allows a simultaneous measurement of fluorescent substances flowing through the channels in the microchemical chip 108.

The probes may be positioned at a plurality of points in the channels in the microchemical chip 108. This enables measuring state of fluorescent substances at a plurality of points.

Although the foregoing embodiments have described the case where a plurality kinds of fluorescent substances is contained in the solution, the plurality kinds of fluorescent substances may be contained in a solid.

A microwell plate is used instead of the microchemical chip 108.

Specifically, the microwell plate is formed in the following manner.

Figure 7A:
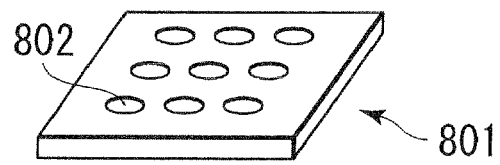
FIGS. 7A to 7E are views describing how to make a microwell plate.
Figure 7B:
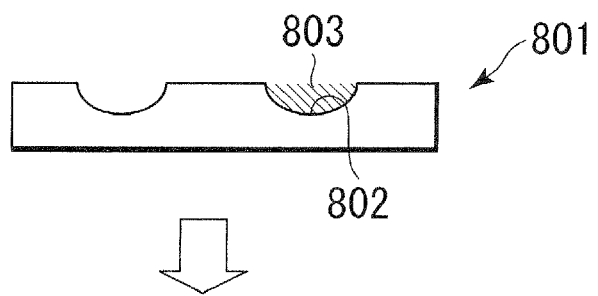
Figure 7C:
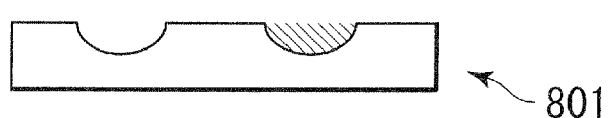
Figure 7D:
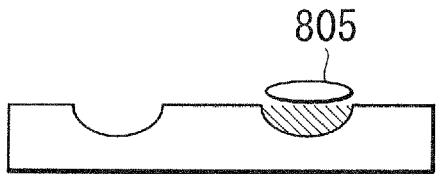

Adsorbent 803 (FIG. 7B) is put into one microwell 802 of a microwell array 801 (FIG. 7A). A liquid sample 805 containing a plurality kinds of fluorescent substances is dropped on the adsorbent 803 using a pipet 804 (refer to FIG. 7C). The liquid sample 805 is caused to adhere to the surface of the adsorbent 803 (refer to FIG. 7D). Thereby, fluorescent substances in the liquid sample 805 are absorbed by the surface of the adsorbent 803.

Figure 7E:
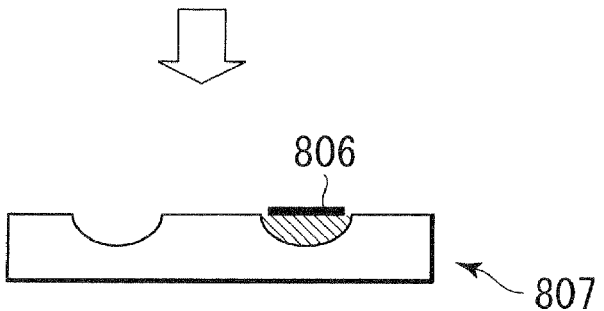

Only liquid on the surface of the adsorbent 803 is absorbed by a dropping pipet (not shown) or paper to remove it, thereby, only the plurality kinds of fluorescent substances 806 is left on the surface of the adsorbent 803 to form a microwell plate 807 (refer to FIG. 7E).

Figure 8:
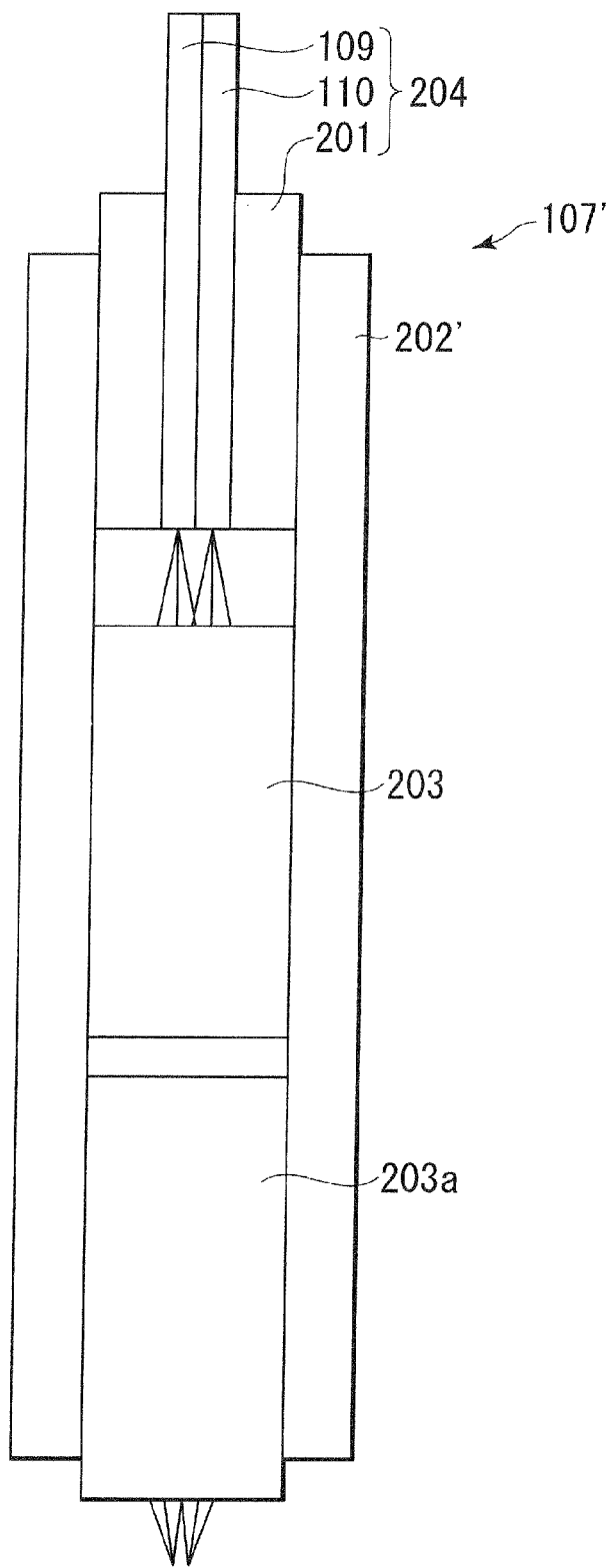
FIG. 8 is a schematic view showing the configuration of a variation of the probe in FIG. 2.
Figure 9:
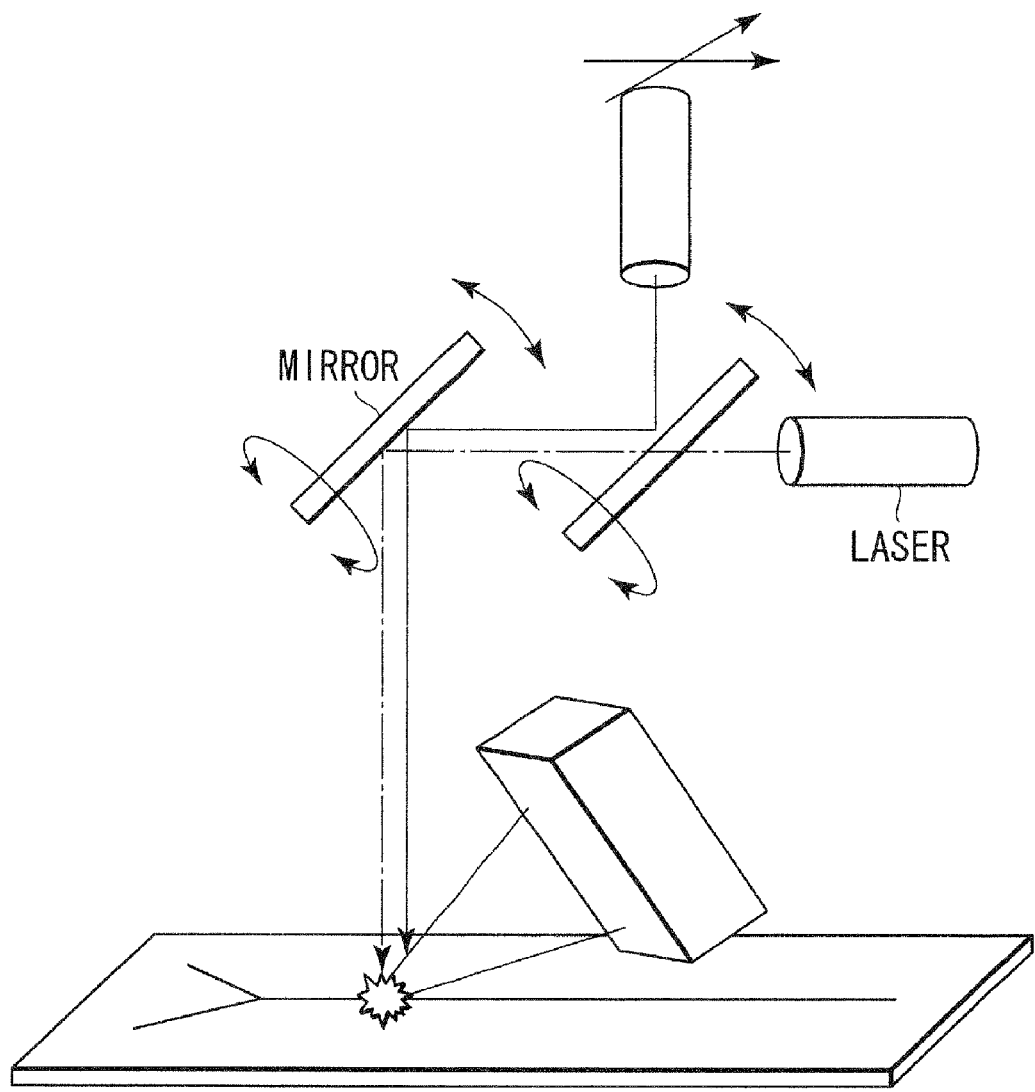
FIG. 9 is a schematic block diagram showing the configuration of a conventional fluorescence detection system.
Figure 10:
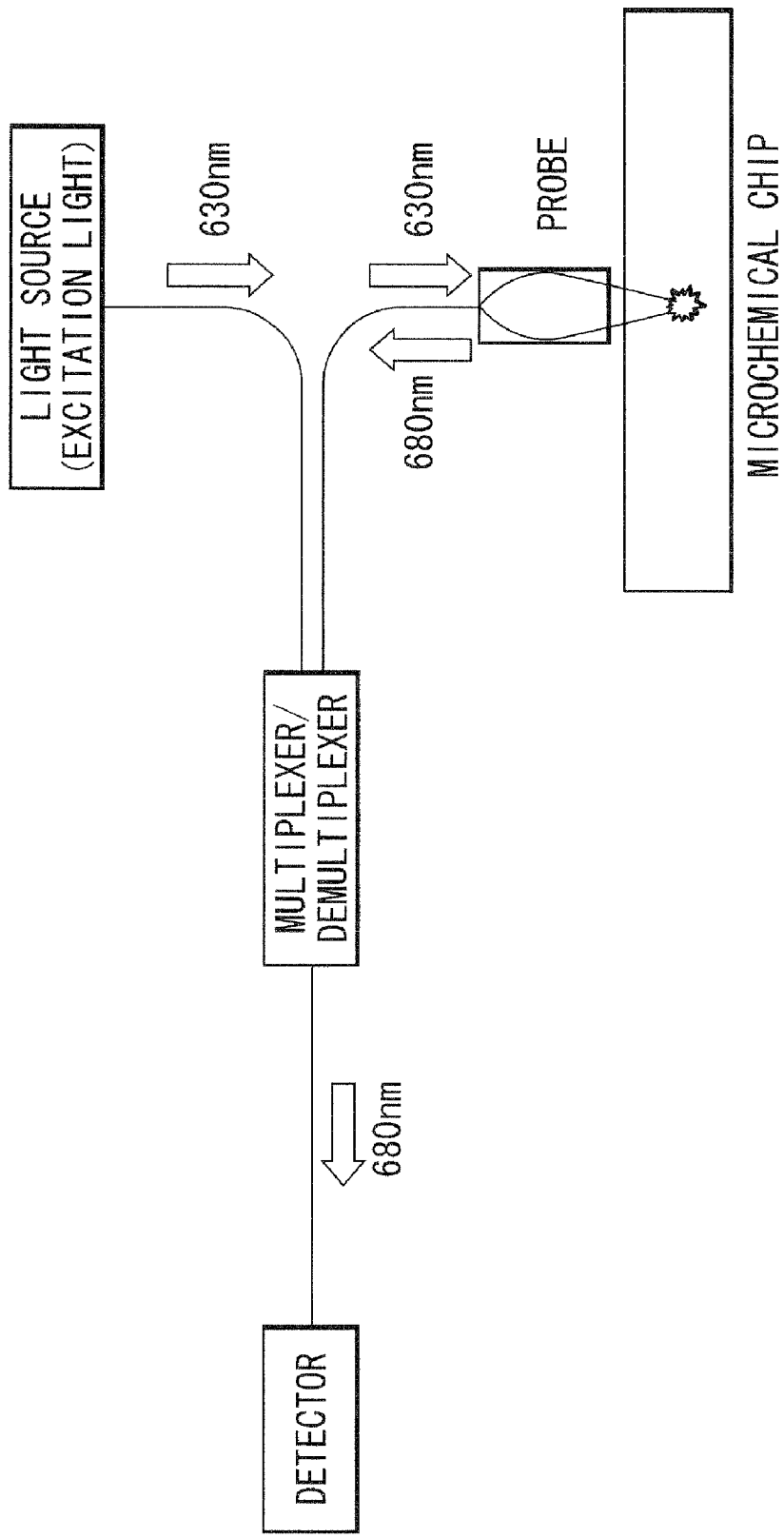
FIG. 10 is a schematic block diagram showing the configuration of another conventional fluorescence detection system.
Figure 11:
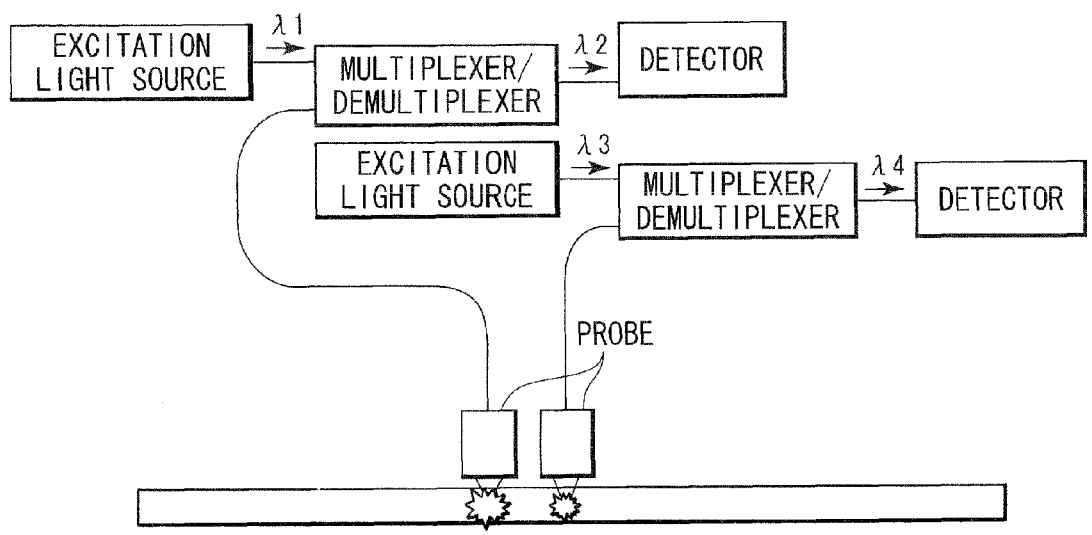
FIG. 11 is a schematic block diagram used for describing how to detect a plurality of fluorescences using the fluorescence detection system in FIG. 10.

In the present embodiment, although the probe 107 has a single SELFOC microlens 203 therein, the probe 107 may use a spherical microlens such as a ball lens or a drum lens. Alternatively, as shown in FIG. 8, a probe 107' may be used in which a microlens 203a is placed on the same optical axis as that of the microlens 203.

The microlens 203a is different from the microlens 203 in Abbe number, which allows reducing chromatic aberrations of the excitation lights propagated by the optical fibers 109 and 110. The microlenses 203 and 203a may be either brought into contact with each other or not if they are on the same optical axis.

Although the foregoing embodiments have described the measurement of a plurality kinds of fluorescent substances contained in the solution, the detection system can also measure a plurality kinds of phosphorescent substances contained in the solution in the similar manner.

INDUSTRIAL APPLICABILITY

According to the present invention, the probe including the lens and at least one optical fiber arranged on one end thereof receives a plurality of the excitation lights at one end of the lens and converges the excitation lights at the solution or the solid and, in addition, the probe receives fluorescence or phosphorescence at the other end of the lens and converges the fluorescence or phosphorescence at the tips of the optical fibers propagating the excitation lights attributed to the occurrence of the fluorescence or phosphorescence, which allows a simultaneous detection of a plurality of fluorescences and phosphorescences with different dominant wavelengths emitted from a minute region.

Preferably, the detection system is provided with a light emitting control unit adapted to control the light emitting timing of the excitation lights and detects fluorescence or phosphorescence based on the light emitting timing, so that the detection system can detect fluorescence or phosphorescence according to change in concentration when a plurality kinds of substances in the solution or a solid sequentially changes in concentration.

Preferably, at least one optical fiber is comprised of an optical fiber propagating the fluorescence or the phosphorescence with dominant wavelengths different from each other. Since the optical fiber propagates the excitation light with dominant wavelengths different from each other to one end of the lens out of the excitation lights, the optical fiber propagating the excitation light also propagates the fluorescence or the phosphorescence generated by irradiating the solution or the solid with the excitation lights to enable the system to be downsized.

Preferably, since at least one optical fiber is comprised of one optical fiber propagating all the excitation lights to the one end of the lens, the optical fiber propagating all the excitation lights also propagates all the fluorescences or the phosphorescences generated by irradiating the solution or the solid with the excitation lights to enable the system to be downsized.

Preferably, the detection system is provided with a light emitting frequency control unit adapted to control the light emitting frequencies of the excitation lights and detects respectively fluorescence or phosphorescence propagated to one detection unit based on the light emitting frequencies, which allows a simultaneous detection of the fluorescence or phosphorescence generated from two kinds of substances.

Preferably, anti-reflection coating is applied on the tip of at least one optical fiber or the tip of at least one optical fiber is fabricated such as to form an angled facet to enable preventing the excitation lights from being reflected at the tip.

Preferably, since the chromatic aberration of the excitation light converged by the lens is less than 0.1 mm, the excitation lights can be surely converged in the channel of the microchemical chip which is generally formed by wet etching in a depth of 0.1 mm or less.

Preferably, since the tips of the optical fibers propagating the excitation lights with dominant wavelengths different from each other are fixed to abut on each other, the displacement of focal point of light outputted from the optical fibers can fall within the range of 0.1 mm in the direction perpendicular to the optical axis direction of the lens, which surely enables each excitation light to be converged in the channel of the microchemical chip formed at a width of typically 0.5 mm or less.

Preferably, since an image in the optical fiber formed by the lens is a reduction system which is smaller than 1:1, a distance from the other end of the lens to a position where each excitation light is converged can be made shorter than a distance from one end of the lens to the tip of each the optical fiber.

The invention claimed is:

1. A detection system in which a plurality of kinds of substances in a solution or solid are irradiated with excitation lights with dominant wavelengths different from each other so as to be excited to generate fluorescence or phosphorescence, and the fluorescence or phosphorescence with dominant wavelengths different from each other generated from the solution or solid in a relaxation process is detected to measure a concentration or state of the plurality of kinds of substances, the detection system comprising a probe including a lens and a plurality of optical fibers arranged on a first end of the lens, the optical fibers propagating therethrough the fluorescence or phosphorescence with dominant wavelengths different from each other, wherein said probe receives the excitation lights at the first end of the lens and converges the excitation lights at the solution or the solid, and said probe receives the fluorescence or phosphorescence at a second end of the lens and converges the fluorescence or phosphorescence at tips of the plurality of optical fibers propagating therethrough the excitation lights attributed to the occurrence of the fluorescence or phosphorescence, wherein the lens comprises a single lens or a plurality of lenses arranged on a same optical axis, and wherein the plurality of optical fibers propagate therethrough the excitation lights with dominant wavelengths different from each other to the first end of the lens, and the plurality of optical fibers propagate the excitation lights and the fluorescence or phosphorescence to detectors different from each other through multiplexers/demultiplexers adapted to separate the excitation lights and the fluorescence or phosphorescence.

2. The detection system according to claim 1, further comprising a light emitting control unit adapted to control a light emitting timing of the excitation lights to detect the fluorescence or phosphorescence based on the light emitting timing.

3. The detection system according to claim 1, wherein the plurality of optical fibers are connected to a plurality of detectors through a multiplexer/demultiplexer adapted to separate the propagated fluorescence or phosphorescence by dominant wavelength.

4. A probe used in a detection system in which a plurality of kinds of substances in a solution or solid are irradiated with excitation lights with dominant wavelengths different from each other so as to be excited to generate fluorescence or phosphorescence, and the fluorescence or phosphorescence with dominant wavelengths different from each other generated from the solution or solid in a relaxation process is detected to measure a concentration or state of the plurality of kinds of substances, the probe including a lens and two optical fibers arranged on a first end of said lens, the two optical fibers propagating therethrough the fluorescence or phosphorescence with dominant wavelengths different from each other, wherein the probe receives the excitation lights at the first end of said lens and converges the excitation lights at the solution or the solid, and the probe receives the fluorescence or phosphorescence at a second end of said lens and converges the fluorescence or phosphorescence at tips of said two optical fibers propagating therethrough the excitation lights attributed to the occurrence of the fluorescence or phosphorescence, wherein the lens comprises a single lens or a plurality of lenses arranged on a same optical axis, wherein the two optical fibers propagate therethrough the excitation lights with dominant wavelengths different from each other to the first end of said lens, and wherein the two optical fibers include a first optical fiber propagating therethrough fluorescence or phosphorescence with a first dominant wavelength generated from one of the plurality of kinds of substances and a second optical fiber propagating therethrough fluorescence or phosphorescence with a second dominant wavelength generated from another of the plurality of kinds of substances.

5. The probe according to claim 4, wherein a chromatic aberration of the excitation light converged by said lens is less than 0.1 mm.

6. The probe according to claim 4, wherein an anti-reflection coating is applied on the tips of the two optical fibers.

7. The probe according to claim 4, wherein the tips of the two optical fibers are fabricated so as to form an angled facet.

8. The probe according to claim 4, wherein the tips of the two optical fibers are fixed to abut on each other.

9. The probe according to claim 4, wherein each of images in the two optical fibers formed by said lens is a reduction system which is smaller than 1:1.

* * * * *